(12) United States Patent
Henschel et al.

(10) Patent No.: US 12,237,281 B2
(45) Date of Patent: Feb. 25, 2025

(54) ELECTRONIC PACKAGE AND IMPLANTABLE MEDICAL DEVICE INCLUDING SAME

(71) Applicant: Medtronic, Inc., Minneapolis, MN (US)

(72) Inventors: Mark E. Henschel, Phoenix, AZ (US); Songhua Shi, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 605 days.

(21) Appl. No.: 17/469,098

(22) Filed: Sep. 8, 2021

(65) Prior Publication Data

US 2022/0077085 A1 Mar. 10, 2022

Related U.S. Application Data

(60) Provisional application No. 63/076,042, filed on Sep. 9, 2020.

(51) Int. Cl.
*H01L 21/00* (2006.01)
*H01L 21/768* (2006.01)
(Continued)

(52) U.S. Cl.
CPC ........ *H01L 24/02* (2013.01); *H01L 21/76898* (2013.01); *H01L 23/481* (2013.01); *H01L 24/06* (2013.01); *A61N 1/3754* (2013.01); *H01L 24/05* (2013.01); *H01L 24/13* (2013.01); *H01L 2224/02371* (2013.01);
(Continued)

(58) Field of Classification Search
CPC . H01L 24/02; H01L 21/76898; H01L 23/481; H01L 24/06
See application file for complete search history.

(56) References Cited

U.S. PATENT DOCUMENTS 10,124,559 B2 * 11/2018 Sandlin .................. B23K 20/22
11,031,345 B2 * 6/2021 Kim ........................ H01L 24/82
(Continued)

FOREIGN PATENT DOCUMENTS

CN 112601580 A * 4/2021 ............. A61N 1/375
CN 112930596 A * 6/2021 ......... H01L 21/4853
(Continued)

OTHER PUBLICATIONS

International Search Report and Written Opinion for PCT/US2021/049386 mailed Jan. 7, 2022 (8 pages).
(Continued)

*Primary Examiner* — Laura M Menz
(74) *Attorney, Agent, or Firm* — Mueting Raasch Group (57) ABSTRACT

Various embodiments of an electronic package and an implantable medical device that includes such package are disclosed. The electronic package includes a monolithic package substrate having a first major surface and a second major surface, an integrated circuit disposed in an active region of the package substrate, and a conductive via disposed through an inactive region of the package substrate and extending between the first major surface and the second major surface of the package substrate. The conductive via is separated from the active region by a portion of the inactive region of the substrate.

20 Claims, 6 Drawing Sheets

(51) Int. Cl.
*H01L 23/00* (2006.01)
*H01L 23/48* (2006.01)
*A61N 1/375* (2006.01)

(52) U.S. Cl.
CPC ............. *H01L 2224/02372* (2013.01); *H01L 2224/02381* (2013.01); *H01L 2224/05024* (2013.01); *H01L 2224/05569* (2013.01); *H01L 2224/05573* (2013.01); *H01L 2224/06182* (2013.01); *H01L 2224/13026* (2013.01)

(56) References Cited

U.S. PATENT DOCUMENTS

| | | | | |
|---|---|---|---|---|
| 11,270,920 | B2 * | 3/2022 | Kim | H01L 24/14 |
| 11,569,178 | B2 * | 1/2023 | Kim | A61N 1/375 |
| 11,876,026 | B2 * | 1/2024 | Kim | H01L 24/19 |
| 2010/0244241 | A1 * | 9/2010 | Marimuthu | H01L 21/56 |
| | | | | 257/737 |
| 2013/0147055 | A1 * | 6/2013 | Na | H01L 21/568 |
| | | | | 257/774 |
| 2014/0027889 | A1 * | 1/2014 | Boone | H01L 29/402 |
| | | | | 257/668 |
| 2014/0252579 | A1 * | 9/2014 | Chang | H01L 23/481 |
| | | | | 257/676 |
| 2020/0058567 | A1 * | 2/2020 | Kim | H01L 21/56 |
| 2020/0058592 | A1 * | 2/2020 | Kim | H01L 21/4857 |
| 2020/0111765 | A1 * | 4/2020 | Kim | H01L 21/4853 |
| 2020/0154567 | A1 * | 5/2020 | Kim | H05K 1/115 |
| 2021/0187307 | A1 * | 6/2021 | Ries | A61N 1/3754 |
| 2021/0272909 | A1 * | 9/2021 | Kim | H01L 23/49827 |
| 2022/0032018 | A1 * | 2/2022 | Sutanto | A61M 39/22 |
| 2022/0077085 | A1 * | 3/2022 | Henschel | H01L 21/76898 |
| 2022/0157676 | A1 * | 5/2022 | Kim | H01L 23/08 |
| 2022/0241598 | A1 * | 8/2022 | Henschel | A61N 1/3756 |
| 2022/0262783 | A1 * | 8/2022 | Yu | H01L 25/0652 |
| 2022/0301890 | A1 * | 9/2022 | Chen | H01L 21/78 |
| 2022/0336393 | A1 * | 10/2022 | Chen | H01L 24/80 |
| 2023/0248982 | A1 * | 8/2023 | Ries | A61N 1/3754 |
| | | | | 607/2 |
| 2023/0378012 | A1 * | 11/2023 | Yeh | H01L 24/20 |
| 2023/0420383 | A1 * | 12/2023 | Crutchfield | H01L 21/76895 |
| 2024/0145322 | A1 * | 5/2024 | Kim | H01L 23/49844 |

FOREIGN PATENT DOCUMENTS

| | | | | |
|---|---|---|---|---|
| CN | 116056756 A | * | 5/2023 | A61N 1/3758 |
| EP | 2761653 A1 | * | 8/2014 | H01L 23/49816 |
| EP | 2761653 B1 | * | 5/2016 | H01L 23/49816 |
| EP | 3837006 A1 | * | 6/2021 | A61N 1/375 |
| EP | 3837716 A1 | * | 6/2021 | H01L 21/4853 |
| EP | 3837006 B1 | * | 9/2023 | A61N 1/375 |
| WO | WO-2013048620 A1 | * | 4/2013 | H01L 23/49816 |
| WO | WO-2020036901 A1 | * | 2/2020 | A61N 1/375 |
| WO | WO-2020036902 A1 | * | 2/2020 | H01L 21/4853 |
| WO | 2020/076780 | | 4/2020 | |
| WO | WO-2020076780 A1 | * | 4/2020 | H01L 23/315 |
| WO | WO-2020102194 A1 | * | 5/2020 | H01G 9/012 |
| WO | WO-2022055945 A1 | * | 3/2022 | A61N 1/3758 |
| WO | WO-2022232467 A1 | * | 11/2022 | H01L 23/13 |
| WO | WO-2023248083 A1 | * | 12/2023 | H01L 21/76829 |

OTHER PUBLICATIONS

International Preliminary Report on Patentability for PCT/US2021/049386 dated Mar. 23, 2023 (7 pages).
Reis et al., U.S. Appl. No. 62/950,694, filed Dec. 19, 2019.

* cited by examiner

FIG. 7 ly include output circuitry for generating
ELECTRONIC PACKAGE AND IMPLANTABLE MEDICAL DEVICE INCLUDING SAME This application claims the benefit of U.S. Provisional Application No. 63/076,042, filed Sep. 9, 2020, the disclosure of which is incorporated by reference herein in its entirety.

TECHNICAL FIELD

This disclosure generally relates to an electronic package and in particular to an implantable medical device that includes the electronic package.

BACKGROUND

A wide variety of electronic assemblies such as those that are utilized for implantable medical devices (IMDs) employ electronic circuitry, e.g., for providing electrical stimulation of body tissue and/or monitoring a physiologic condition. Such IMDs may deliver electrical therapy energy in the form of shocking energy and stimulating pulses to selected body tissue and typically include output circuitry for generating the electrical energy under prescribed conditions and at least one lead bearing a stimulation electrode for delivering the electrical energy to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle, and organ tissue stimulating medical devices are also known for treating a variety of conditions.

Currently available IMDs, including ICDs and implantable pulse generators (IPGs), are typically formed having a metallic housing that is hermetically sealed and, therefore, is impervious to body fluids, and a header or connector assembly mounted to the housing for making electrical and mechanical connection with one or more leads. Such devices also possess telemetry capabilities for communicating with external devices. Over the past 20 years, IMDs have evolved from relatively bulky devices to complex miniaturized devices that exhibit increasing functionality. For example, numerous improvements have been made in cardioversion/defibrillation leads and electrodes that have enabled the cardioversion/defibrillation energy to be precisely delivered to selected one or more portions of upper and lower heart chambers such that the delivered shock energy required to cardiovert or defibrillate the heart chamber has been reduced. High voltage output circuitry has also been improved in many respects to provide monophasic, biphasic, or multi-phase cardioversion/defibrillation shock or pulse waveforms that are efficacious, sometimes with particular combinations of cardioversion/defibrillation electrodes, in lowering the required shock energy to cardiovert or defibrillate the heart.

The miniaturization of IMDs is driving size and cost reduction of all IMD components, including the electronic circuitry components, where it is desirable to increase the density and reduce the size of such components so that the overall circuitry can be more compact. As the dimensions of IMDs decrease, the electronic circuits of the IMD are formed as integrated circuits to fit within a minimal space. Furthermore, as the dimensions of the components are also being reduced, it is desirable to improve the use of the dimensions within the IMD package. One response to this desire has been through technological improvements to the packaging for the devices in which the output circuitry is included through such packaging techniques as embedded integrated circuits.

SUMMARY

The techniques of this disclosure generally relate to various embodiments of electronic packages and devices and systems that utilize such packages. One embodiment of an electronic package can include a via disposed through an inactive region of a package substrate. The via can be separated from an active region of the package substrate by a portion of the inactive region. Such active region can include one or more integrated circuits that can be electrically connected to the via by a patterned conductive layer disposed adjacent to at least one of a first major surface or a second major surface of the package substrate.

This disclosure includes without limitation the following clauses:

Clause 1: In one example, aspects of this disclosure relate to an electronic package that includes a monolithic package substrate having a first major surface and a second major surface, an integrated circuit disposed in an active region of the package substrate, and a conductive via disposed through an inactive region of the package substrate and extending between the first major surface and the second major surface of the package substrate. The conductive via is separated from the active region by a portion of the inactive region of the substrate.

Clause 2: The package of clause 1, further including a patterned conductive layer disposed adjacent to at least one of the first major surface and the second major surface of the package substrate and electrically connected to the conductive via and the integrated circuit.

Clause 3: The package of clause 2, where the patterned conductive layer is disposed adjacent to the first major surface of the substrate, and where the package further includes a second patterned conductive layer disposed adjacent to the second major surface of the substrate and electrically connected to the conductive via.

Clause 4: The package of any one of clauses 2-3, further including a dielectric layer disposed between the patterned conductive layer and the first major surface of the package substrate.

Clause 5: The package of any one of clauses 2-4, further including a dielectric layer disposed between the second patterned conductive layer and the second major surface of the package substrate.

Clause 6: The package of any one of clauses 1-5, where the active region takes a rectangular shape in a plane parallel to the first major surface of the package substrate, where the inactive region further includes a second portion, and where the portion and second portion of the inactive region are disposed on opposing sides of the active region in the plane parallel to the first major surface of the package substrate.

Clause 7: The package of any one of clauses 1-6, further including a second conductive via disposed through the inactive region of the package substrate and extending between the first major surface and the second major surface of the package substrate, where the second conductive via is separated from the active region by the second portion of the inactive region of the substrate.

Clause 8: The package of any one of clauses 1-7, where the active region is embedded within the inactive region such that the active region is surround by the inactive region in a plane parallel to the first major surface of the package substrate.

Clause 9: The package of any one of clauses 1-8, where the conductive via extends in a direction substantially orthogonal to the first and second major surfaces of the substrate.

Clause 10: The package of any one of clauses 1-9, further including a guard ring disposed in the first major surface of substrate, where the guard ring circumscribes the active region and the integrated circuit.

Clause 11: The package of any one of clauses 1-10, where the conductive via includes a dielectric layer disposed on one or more walls of the via.

Clause 12: The package of clause 11, where the conductive via further includes conductive material disposed in the via such that the dielectric material is between the conductive material and the one or more walls of the via.

Clause 13: The package of clause 12, where the conductive via further includes insulating material disposed within the via such that the conductive material is disposed between the one or more walls of the via and the insulating material.

Clause 14: The package of any one of clauses 1-13, where the integrated circuit includes at least one of a field effect transistor (FET), metal oxide semiconductor (MOS), MOSFET, insulated gate bipolar junction transistor (IGBT), thyristor, bipolar transistor, diode, MOS-controlled thyristor, resistor, capacitor, inductor, sensor-mixed signal application-specific integrated circuit (ASIC), digital circuit, or analog circuit.

Clause 15: The package of any one of clauses 1-14, further including a conductive pillar disposed within the conductive via and electrically connected to the integrated circuit.

Clause 16: The package of any one of clauses 1-15, further including a conductive pad disposed on either the first major surface or the second major surface of the substrate and electrically connected to the integrated circuit.

Clause 17: In another example, aspects of this disclosure relate to a wafer that includes a wafer substrate and a plurality of electronic packages disposed on the wafer substrate. Each electronic package includes a package substrate formed from the wafer substrate and having a first major surface and a second major surface, an integrated circuit disposed in an active region of the package substrate, and a conductive via disposed through an inactive region of the package substrate and extending between the first major surface and the second major surface of the package substrate. The conductive via is separated from the active region by a portion of the inactive region of the substrate.

Clause 18: The wafer of clause 17, where each electronic package further includes a patterned conductive layer disposed adjacent to at least one of the first major surface and the second major surface of the package substrate and electrically connected to the conductive via and the integrated circuit.

Clause 19: The wafer of clause 18, where the patterned conductive layer is disposed adjacent to the first major surface of the substrate, and where each package further includes a second patterned conductive layer disposed adjacent to the second major surface of the substrate and electrically connected to the conductive via.

Clause 20: The wafer of any one of clauses 18-19, where each electronic package further includes a dielectric layer disposed between the patterned conductive layer and the first major surface of the package substrate.

Clause 21: The wafer of any one of clauses 18-20, where each electronic package further includes a dielectric layer disposed between the second patterned conductive layer and the second major surface of the package substrate.

Clause 22: The wafer of any one of clauses 17-21, where the active region of each electronic package takes a rectangular shape in a plane parallel to first major surface of the package substrate, where the inactive region further includes a second portion, and where the portion and second portion of the inactive region are disposed on opposing sides of the active region in the plane parallel to the first major surface of the package substrate.

Clause 23: The wafer of any one of clauses 17-22, where each electronic package further includes a second conductive via disposed through the inactive region of the package substrate and extending between the first major surface and the second major surface of the package substrate, and where the second conductive via is separated from the active region by the second portion of the inactive region of the substrate.

Clause 24: The wafer of any one of clauses 17-23, where the active region of each electronic package is embedded within the inactive region such that the active region is surround by the inactive region in a plane parallel to the first major surface of the package substrate.

Clause 25: The wafer of any one of clauses 17-24, where the conductive via of each electronic package extends in a direction substantially orthogonal to the first and second major surfaces of the substrate.

Clause 26: The wafer of anyone of clauses 17-25, where each electronic package further includes a guard ring disposed in the first major surface of the package substrate, and where the guard ring circumscribes the active region and the integrated circuit.

Clause 27: The wafer of any one of clauses 17-26, where the conductive via includes a dielectric layer disposed on one or more walls of the via.

Clause 28: The wafer of clause 27, where the conductive via further includes conductive material disposed in the via such that the dielectric material is between the conductive material and the one or more walls of the via.

Clause 29: The wafer of clause 28, where the conductive via further includes insulating material disposed within the via such that the conductive material is disposed between the one or more walls of the via and the insulating material.

Clause 30: The wafer of any one of clauses 17-29, where the integrated circuit of each package includes at least one of a field effect transistor (FET), metal oxide semiconductor (MOS), MOSFET, insulated gate bipolar junction transistor (IGBT), thyristor, bipolar transistor, diode, MOS-controlled thyristor, resistor, capacitor, inductor, sensor-mixed signal application-specific integrated circuit (ASIC), digital circuit, or analog circuit.

Clause 31: The wafer of any one of clauses 17-30, further including a conductive pillar disposed within the conductive via of each package and electrically connected to the integrated circuit.

Clause 32: The wafer of any one of clauses 17-31, wherein each package further includes a conductive pad disposed on either the first major surface or the second major surface of the substrate and electrically connected to the integrated circuit.

Clause 33: In another example, aspects of this disclosure relate to an implantable medical device that includes a power source and an electronics module that includes an electronic package. The electronic package includes a monolithic package substrate having a first major surface and a second major surface, an integrated circuit disposed in an active region of the package substrate, and a conductive via disposed through an inactive region of the package substrate and extending between the first major surface and the second major surface of the package substrate. The conductive via is separated from the active region by a portion of the inactive region of the substrate. The implantable medical device also includes a feedthrough header assembly electrically connected to the electronics module.

Clause 34: The device of clause 33, further including an elongated tubular housing extending between a first end and a second end along a longitudinal axis, where a first portion of the housing adjacent to the first end encloses the electronics module and a second portion of the housing adjacent to the second end encloses the power source.

Clause 35: The device of clause 33, where the active region of the electronic package takes a rectangular shape in a plane parallel to the first major surface of the package substrate, and where the inactive region further includes a second portion, where the portion and second portion of the inactive region are disposed on opposing sides of the active region in the plane parallel to the first major surface of the package substrate.

Clause 36: The device of clause 35, where the electronic package further includes a second conductive via disposed through the inactive region of the package substrate and extending between the first major surface and the second major surface of the package substrate, where the second conductive via is separated from the active region by the second portion of the inactive region of the substrate.

Clause 37: In another example, aspects of this disclosure relate to a method that includes disposing an active region in a wafer substrate, disposing an integrated circuit within the active region of the wafer substrate, and disposing a patterned conductive layer adjacent to a first major surface of the wafer substrate, where the patterned conductive layer is electrically connected to the integrated circuit. The method further includes disposing a conductive via through an inactive region of the wafer substrate that extends between the first major surface of the wafer substrate and a second major surface of the wafer substrate, where the conductive via is separated from the active region by a portion of the inactive region of the wafer substrate; and disposing conductive material within the conductive via to form a conductive via, where the conductive material is electrically connected to the patterned conductive layer.

Clause 38: The method of clause 37, further including disposing a conductive pad on the patterned conductive layer.

Clause 39: The method of any one of clauses 37-38, further including disposing a dielectric layer on the patterned conductive layer.

Clause 40: The method of any one of clauses 37-39, further including disposing a carrier over the patterned conductive layer prior to disposing the conductive via through the inactive region of the wafer substrate.

Clause 41: The method of any one of clauses 37-40, further including removing a portion of the second major surface of the wafer substrate prior to disposing the conductive via through the inactive region of the wafer substrate.

Clause 42: The method of any one of clauses 37-41, further including disposing a second patterned conductive layer adjacent to the second major surface of the wafer substrate after disposing the conductive via through the inactive region of the wafer substrate.

Clause 43: The method of clause 42, further including disposing dielectric material over the second patterned conductive layer.

Clause 44: The method of any one of clauses 37-43, further including singulating the wafer substrate to form an electronic package.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 4A-J are schematic cross-section views of one embodiment of a method of forming the electronic package of FIG. 1, where

DETAILED DESCRIPTION

The techniques of this disclosure generally relate to various embodiments of electronic packages and devices and systems that utilize such packages. One embodiment of an electronic package can include a via disposed through an inactive region of a package substrate. The via can be separated from an active region of the package substrate by a portion of the inactive region. Such active region can include one or more integrated circuits that can be electrically connected to the via by a patterned conductive layer disposed adjacent to at least one of a first major surface or a second major surface of the package substrate.

Electronic packages that included embedded integrated circuits utilize one or more vias that extend through a substrate of the package to an active area or region of the substrate where the integrated circuit has been formed. Such vias, therefore, extend into the active region. These vias, however, can only be formed when fabricating the integrated circuit and not afterward.

One or more embodiments of electronic packages described herein can include vias that are formed such that they are spaced apart from an active region of a substrate of the package by one or more portions of an inactive region of the substrate. By placing the vias outside of the active region, an overall thickness of the package can be reduced. Further, such vias can be formed after the integrated circuit has been disposed in the active region of the substrate.

Figure 1:
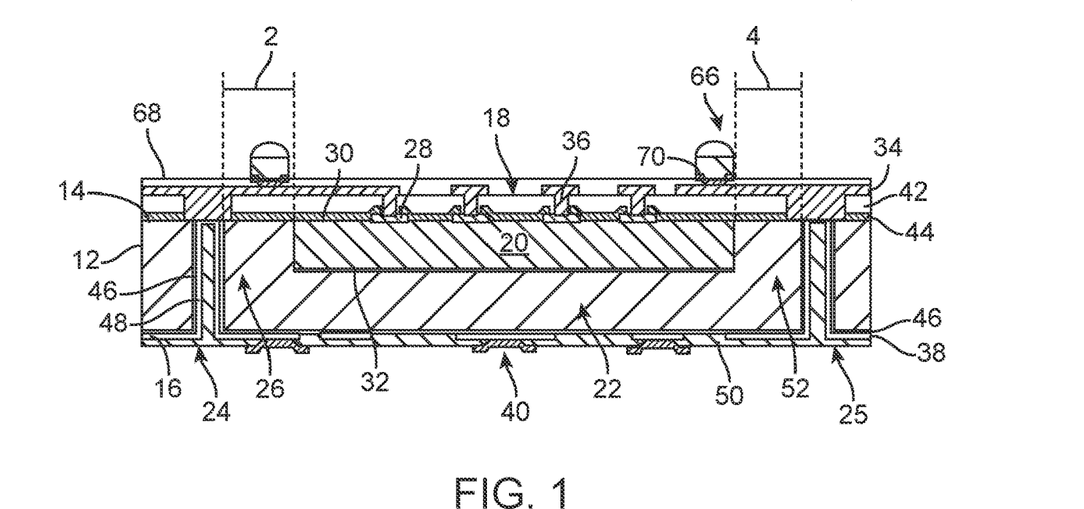
FIG. 1 is a schematic cross-section view of one embodiment of an electronic package.
Figure 2:
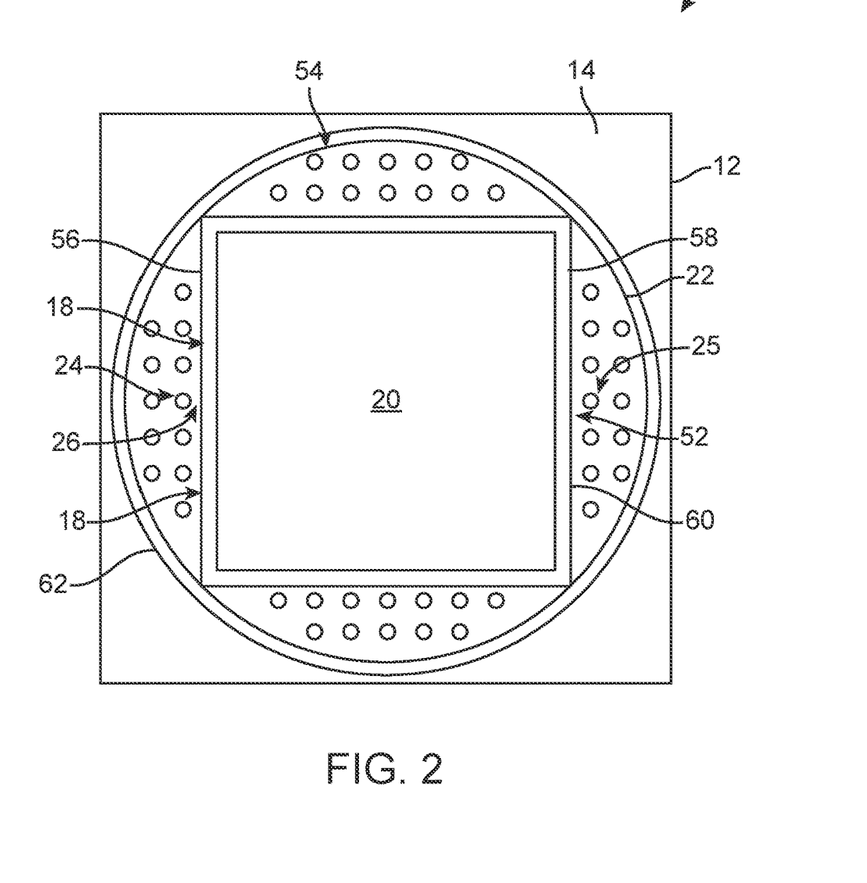
FIG. 2 is a schematic plan cross-section view of the electronic package of FIG. 1.

FIGS. 1-2 are schematic cross-section views of one embodiment of an electronic package 10. The electronic package 10 includes a monolithic package substrate 12 that includes a first major surface 14 and a second major surface 16. The package substrate 12 also includes an active region 18. An integrated circuit 20 is disposed in the active region 18. The substrate 12 further includes an inactive region 22. The package 10 also includes a conductive via 24 disposed through the inactive region 22 of the package substrate 12, where the via extends between the first major surface 14 and the second major surface 16 of the package substrate 12. The conductive via 24 is separated from the active region 18 by a portion 26 of the inactive region 22 of the substrate 12.

The substrate 12 of the package 10 can include any suitable material or materials, e.g., metallic, polymeric, or inorganic materials, or combinations thereof. In one or more embodiments, the substrate 12 can be a nonconductive or dielectric substrate that provides electrical isolation between various conductors, vias, dies, etc. In one or more embodiments, the substrate 12 can include a semiconductive material or materials. In one or more embodiments, the substrate can include at least one of silicon, germanium, gallium arsenide, silicon carbide, gallium nitride, gallium phosphide, cadmium sulfide, lead sulfide, or polymer semiconductors.

For convenience and without intending to be limiting, FIG. 1 depicts the substrate 12 as a monolithic (i.e., single) layer. In one or more embodiments, the substrate 12 can include any suitable number of layers, where the layers can be formed from the same or different materials. Further, the substrate 12 can have any suitable dimensions. For example, the substrate 12 can have any suitable thickness as measured in a direction orthogonal to the first and second major surfaces 14, 16. Further, the substrate 12 can be formed using any suitable technique or techniques.

The package substrate 12 includes the active region 18 and the inactive region 22. As used herein, the term "active region" means a portion or portions of the substrate where one or more integrated circuits are formed. Further, as used herein, the term "inactive region" means a portion or portions of the substrate that do not include any integrated circuits. Although depicted as including one active region 18, the substrate 12 can include any suitable number of active regions, e.g., one, two, three, four, five, or more active regions disposed in any suitable arrangement or pattern. Further, each active region 18 can take any suitable shape or shapes and have any suitable dimensions. In one or more embodiments, the active region 18 can take a rectangular shape in a plane parallel to the first major surface 14 of the package substrate 12. The active region 18 can be disposed on or in any suitable portion of the substrate 12. Further, the active region 18 can be formed using any suitable integrated circuitry fabrication techniques.

The substrate 12 can also include any suitable number of inactive regions 22, e.g., one, two, three, four, five, or more inactive regions. Each inactive region 22 can take any suitable shape or shapes and have any suitable dimensions. In general, the inactive region 22 includes a portion or portions of the substrate 12 that do not include active regions. As a result, the inactive region 22 can have any spatial relationship with the active region 18. For example, the active region 18 can be disposed in the inactive region 22 such that the active region is surrounded by the inactive region in a plane parallel to the first major surface of the substrate 12. Further, for example, one or more inactive regions 22 can be disposed in an active region 18 such that the one or more inactive regions are surrounded by the active region.

The active region 18 of the substrate 12 includes an integrated circuit 20. The integrated circuit 20 can include any suitable electronic elements or devices, e.g., at least one of an active or a passage device. In one or more embodiments, the integrated circuit 20 can include at least one of a field effect transistor (FET), metal oxide semiconductor (MOS), MOSFET, insulated gate bipolar junction transistor (IGBT), thyristor, bipolar transistor, diode, MOS-controlled thyristor, resistor, capacitor, inductor, sensor-mixed signal application-specific integrated circuit (ASIC), digital circuit, or analog circuit. The various devices of the integrated circuit 20 can be electrically connected using any suitable technique or techniques. Further, one or more conductive pads 28 can be disposed on or in at least one of a first major surface 30 or a second major surface 32 of the active region 18 that are electrically connected to one or more elements or devices of the integrated circuit 20. The conductive pads 28 can take any suitable shape or shapes and have any suitable dimensions. Further, the conductive pads 28 can include any suitable conductive material or materials and be formed using any suitable technique or techniques. The conductive pads 28 can provide one or more electrical connections between the devices of the integrated circuit 20 and one or more devices that are external to the active region 18 of the substrate 12 as is further described herein.

Disposed through the inactive region 22 of the package substrate 12 is the conductive via 24. The package 10 can include any suitable number of conductive vias, e.g., one, two, three, four, five or more conductive vias. As shown in FIG. 1, the package 10 includes the conductive via 24 and a second conductive via 25. In one or more embodiments, the package 10 can include a plurality of vias 54 as shown in FIG. 2. The conductive vias 24, 25 can take any suitable shape or shapes and have any suitable dimensions. In one or more embodiments, the conductive vias 24, 25 extend in a direction substantially orthogonal to the first and second major surfaces 14, 16 of the package substrate 12. The conductive vias 24, 25 can be disposed through the substrate 12 using any suitable technique or techniques. Further, the conductive vias 24, 25 can include any suitable conductive material or materials 48. In one or more embodiments, at least one of the conductive via 24 or the second conductive via 25 includes a conductive pillar disposed within the conductive via. As shown in FIG. 1, each of the conductive vias 24, 25 includes a conductive material 48 disposed on one or more walls of the respective via, and an insulating material 50 can be disposed within each via such that the conductive material is disposed between the one or more walls of the via and the insulating material. The insulating material 50 can include any suitable material or materials. Further, in one or more embodiments, a dielectric layer 46 can be disposed on one or more walls of the vias 24, 25 such that the dielectric layer is between the conductive material 48 and the one or more walls.

Each of the conductive vias 24, 25 can be disposed in any suitable portion of the substrate 12. In the embodiment illustrated in FIG. 1, the conductive via 24 is disposed such that the via is separated from the active region 18 by the portion 26 of the inactive region 22 of the substrate 12. Further, the second conductive via 25 is disposed such that it is separated from the active region 18 by a second portion 52 of the inactive region 22. The portions 26, 52 can take any suitable shape or shapes and have any suitable dimensions. In one or more embodiments, the portion 26 can have a width such that the via 24 is spaced apart from the active region 18 by a length 2. The length 2 is measured between the via 24 and the active region 18 in a plane parallel to the first major surface 14 of the substrate 12. The length 2 can have any suitable value, e.g., at least 5 microns and no greater than 2000 microns. Similarly, the second portion 52 can have a width such that the second via 25 is spaced apart from the active region 18 by a second length 4. The second length 4 is measured between the second via 25 and the active region 18 in the plane parallel to the first major surface 14 of the substrate 12. The second length 4 can have any suitable value, e.g., at least 5 microns and no greater than 2000 microns. The length 2 and the second length 4 can be equal. In one or more embodiments, the length 2 and the second length 4 can have different values.

In one or more embodiments, at least one of the via 24 and the second via 25 can be completely surrounded by one or more portions of the inactive region 22 such that the respective via is isolated from the active region 18. As shown in FIG. 2, the active region 18 takes a rectangular shape in a plane parallel to the first major surface 14 of the package substrate 12. The inactive region 22 of the package substrate 12 includes the portion 26 and the second portion 52. The portion 26 and the second portion 52 of the inactive region 18 are disposed on opposing sides 56, 58 of the active region 18 in the plane parallel to the first major surface 14 of the package substrate 12.

In one or more embodiments, the package 10 can include a patterned conductive layer 34. The patterned conductive layer 34 can include any suitable type of conductive layer or layers, e.g., one or more redistribution layers. The patterned conductive layer 34 can be disposed adjacent to at least one of the first major surface 14 and the second major surface 16 of the package substrate 12. In the embodiment illustrated in FIG. 1, the patterned conductive layer 34 is disposed adjacent to the first major surface 14 of the package substrate 12. As used herein, the term "adjacent to the first major surface" means that the patterned conductive layer 34 is disposed closer to the first major surface 14 of the package substrate 12 than to the second major surface 16 of the package substrate. In one or more embodiments, the patterned conductive layer 34 can be disposed on and in contact with the first major surface 14 of the package substrate 12.

The patterned conductive layer 34 can be electrically connected to at least one of the conductive via 24, the second conductive via 25, or the integrated circuit 20 using any suitable technique or techniques. In one or more embodiments, the patterned conductive layer 34 is electrically connected to at least one of the conductive via 24, the second conductive via 25, or the integrated circuit 20. In the embodiment illustrated in FIG. 1, the patterned conductive layer 34 is electrically connected to conductive pads 28 of integrated circuit 20 through vias 36. Such vias 36 can be formed through one or more dielectric layers that are disposed between the patterned conductive layer 34 and the substrate 12 as is further described herein. The patterned conductive layer 34 can include any suitable conductive material or materials and be formed using any suitable techniques.

In one or more embodiments, the package 10 also includes a second patterned conductive layer 38 disposed adjacent to the second major surface 16 of the package substrate 12. As used herein, the term "adjacent to the second major surface" means that the second patterned conductive layer 38 is disposed closer to the second major surface 16 of the package substrate 12 than to the first major surface 14 of the substrate. The second patterned conductive layer 38 can include any suitable patterned conductive layer or layers, e.g., the same layer as described regarding patterned conductive layer 34. The second patterned conductive layer 38 can, for example, include any suitable type of conductive layer or layers, e.g., one or more redistribution layers. The second patterned conductive layer 38 can be electrically connected to at least one of the conductive via 24, the second conductive via 25, or the integrated circuit 20 using any suitable technique or techniques. In one or more embodiments, one or more conductive pads 40 can be electrically connected to the second patterned conductive layer 38 through one or more dielectric layers as is further described herein.

As shown in FIG. 1, the package 10 also includes a dielectric layer 42 disposed between the patterned conductive layer 34 and the first major surface 14 of the package substrate 12. The dielectric layer 42 can include any suitable material or materials, e.g., polyimide, bismaleimide triazine, polybenzoxazole, photoresist, glass, quartz, sapphire, etc. In one or more embodiments, the dielectric layer 42 includes an electrically insulative material. Further, the dielectric layer 42 can have any suitable dimensions. In one or more embodiments, the dielectric layer 42 can include two or more layers or sublayers, and each sublayer can include the same or different materials. The dielectric layer 42 can be formed using any suitable technique or techniques. In one or more embodiments, dielectric layer 42 can be formed on the substrate 12. In one or more embodiments, the dielectric layer 42 can be formed separately and then connected to the substrate 12, e.g., by laminating the dielectric layer to the substrate.

The dielectric layer 42 can be disposed on or in contact with the first major surface 14 of the package substrate 12. In one or more embodiments, one or more additional layers can be disposed between the dielectric layer 42 and the first major surface 14. For example, as illustrated in FIG. 1, an oxide layer 44 is disposed on and in contact with the first major surface 14 such that it is between the dielectric layer 42 and the first major surface. The oxide layer 44 can include any suitable material or materials and be disposed on and in contact with the first major surface 14 using any suitable technique or techniques.

Further, one or more layers can be disposed between the second patterned conductive layer 38 and the second major surface 16 of the package substrate 12. For example, as shown in FIG. 1, dielectric layer 46 is disposed between the second patterned conductive layer 38 and the second major surface 16. Such dielectric layer 46 can include any suitable dielectric layer or layers, e.g., dielectric layer 42. The dielectric layer 46 can be formed using the same material or materials used for insulating material 48 that is disposed within the via 24. In one or more embodiments, dielectric layer 46 can be disposed on and in contact with the second major surface 16. In one or more embodiments, an additional layer or layers can be disposed between the dielectric layer 46 and the second major surface 16. The dielectric layer 46 can also be disposed within the vias 24, 25 such that the dielectric layer is between the conductive material 48 and one or more walls of the vias.

In the embodiment illustrated in FIGS. 1-2, the package 10 also includes a guard ring 60 (FIG. 2) that is disposed in or on the first major surface 14 of the substrate 12. The guard ring 60 can include any suitable material or materials and take any suitable shape. Further, the guard ring 60 can have any suitable dimensions. In the illustrated embodiment, the guard ring 60 circumscribes the integrated circuit 20 of the package 10. Also shown in FIG. 2 is singulation street 62 along which one or more portions of the substrate 12 can be removed during singulation of the package 10. The singulation street 62 can take any suitable shape or shapes and have any suitable dimensions.

The package 10 can also include additional conductive pads disposed adjacent to at least one of the first major surface 14 and the second major surface 16 of the package substrate 12. As shown in FIG. 1, package 10 includes conductive pads 66 disposed adjacent to the first major surface 14 of the package substrate 12. The package 10 can include any suitable number of conductive pads. The conductive pads 66 can be electrically connected to the patterned conductive layer 34 using any suitable technique or techniques. In one or more embodiments, the conductive pads 66 can be electrically isolated from the patterned conductive layer 34 using any suitable technique or techniques. For example, a dielectric layer 68 can be disposed on the patterned conductive layer 34 between the conductive pads 66 and the patterned conductive layer. The dielectric layer 68 can include any suitable dielectric layer, e.g., dielectric layer 42. One or more vias 70 can be disposed through this dielectric layer 68 such that it electrically connects the conductive pads 66 to the patterned conductive layer 34. The conductive pads 66 can include any suitable conductive pad or element. Further, the conductive pads 66 can include any suitable material materials and be disposed on the pattern conductive layer 34 using any suitable technique or techniques. In one or more embodiments, the conductive pads 66 can be utilized to electrically connect the electronic package to one or more devices or packages.

Figure 3:
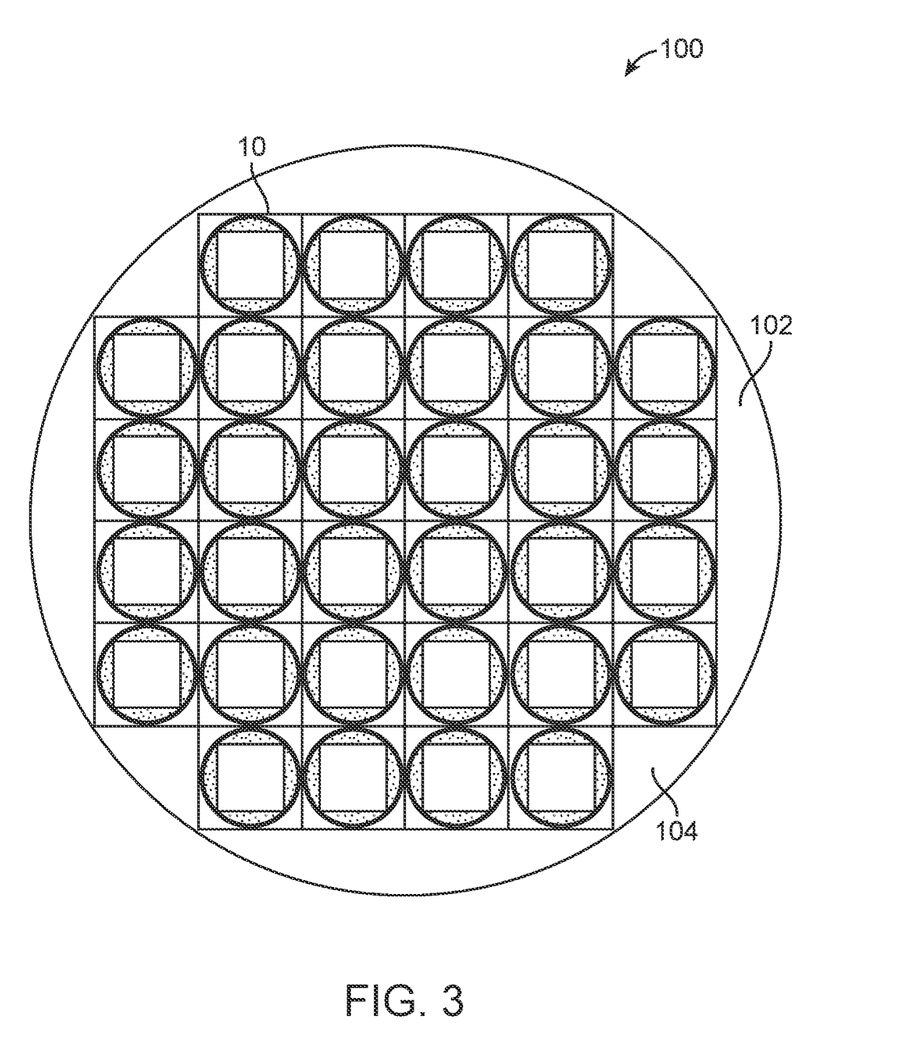
FIG. 3 is a schematic plan cross-section view of a wafer that includes one or more electronic packages of FIG. 1.

The package 10 can be manufactured using any suitable technique or techniques as is further described herein. In one or more embodiments, the package 10 can be formed as part of a wafer 100 as shown in FIG. 3. The wafer 100 includes a wafer substrate 102 and a plurality of electronic packages 104 disposed on or in the wafer substrate. The plurality of electronic packages 104 can include any suitable electronic package or packages. In the embodiment illustrated in FIG. 3, the plurality of electronic packages 104 includes one or more of package 10 of FIG. 1-2. The packages 104 can be disposed in any suitable arrangement on or within the wafer substrate 102. Further, each package 10 can be spaced apart from an adjacent package any suitable distance.

The wafer substrate 102 can include any suitable material or materials, e.g., the same materials described herein regarding the package substrate 12 of package 10 of FIGS. 1-2. In one or more embodiments, the package substrate 12 of each electronic package 10 can be formed from the wafer substrate 102. The wafer substrate 102 can take any suitable shape or shapes and have any suitable dimensions.

Any suitable technique or techniques can be utilized to form the package 10 of FIGS. 1-2. For example, FIGS. 4A-J illustrate one embodiment of a method 200 of manufacturing the package 10. Although the method 200 is described in reference to package 10 of FIGS. 1-2, the method can be utilized to form any suitable package or packages. Further, while FIGS. 4A-J illustrate method 200 as forming a single package 10, such method can be utilized with the wafer 100 of FIG. 3 to form a plurality of packages on or within the wafer substrate 102 in the same process.

Figure 4A:
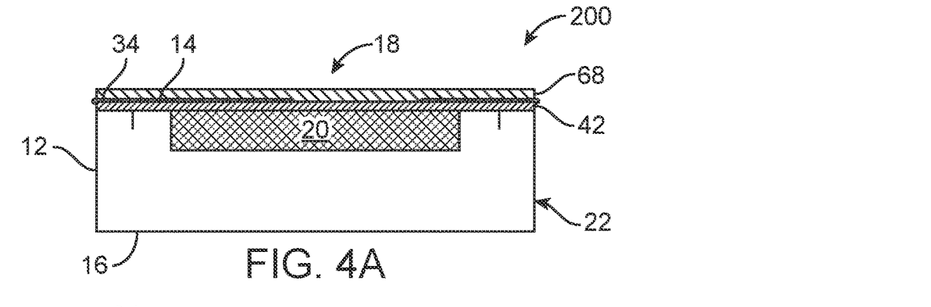
FIG. 4A is a schematic cross-section view of an integrated circuit formed in an active region of a package substrate.

In FIG. 4A, the active region 18 is disposed in the package substrate 12 (or wafer substrate 102) using any suitable technique or techniques. The integrated circuit 20 can also be disposed within the active region 18 of the substrate 12 using any suitable technique or techniques. Further, the patterned conductive layer 34 can be disposed adjacent to the first major surface 14 of the substrate 12 using any suitable technique or techniques. One or more dielectric layers such as dielectric layer 42 and dielectric layer 68 of FIG. 1 can be disposed between the pattern conductive layer 34 and the first major surface 14 of the substrate 12 or on the patterned conductive layer using any suitable technique or techniques.

Figure 4B:
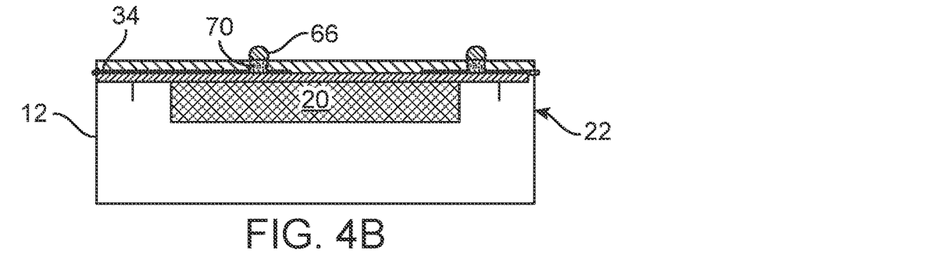
FIG. 4B is a schematic cross-section view of conductive pads or bumps disposed on a patterned conductive layer.

As shown in FIG. 4B, the conductive pads 66 can be disposed through the dielectric layer 68 and dielectric layer 42 such that they are electrically connected to the pattern conductive layer 34. Such conductive pads 66 can be electrically connected to the patterned conductive layer 34 using any suitable technique or techniques. For example, one or more vias 70 can be disposed through the dielectric layer 68 such that they extend between the conductive pads 66 and the patterned conductive layer 34 and electrically connect the pads to the patterned conductive layer.

Figure 4C:
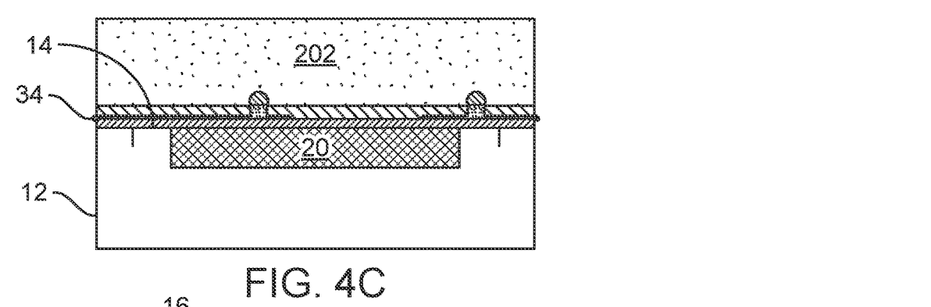
FIG. 4C is a schematic cross-section view of a carrier disposed on the conductive pads and the patterned conductive layer.

A nonconductive carrier 202 can be disposed over the first major surface 14 of the package substrate 12 using any suitable technique or techniques as shown in FIG. 4C. Such nonconductive carrier 202 can include any suitable material or materials, e.g., at least one of glass, sapphire, silicon, or ceramic material. In one or more embodiments, the nonconductive carrier 202 can protect the conductive pads 66, the patterned conductive layer 34, and the active region 18 while further processing is performed. The nonconductive carrier 202 can, in one or more embodiments, include a nonconductive wafer that is disposed over the first major surface 14 of each of a plurality of electronic packages 10.

Figure 4D:
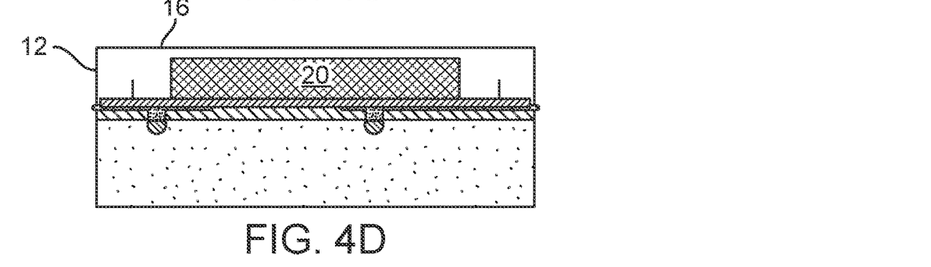
FIG. 4D is a schematic cross-section view of a portion of the package substrate removed from the substrate.

One or more portions of the substrate 12 (or the wafer substrate 102) can be removed to reduce a thickness of the package 10 as shown in FIG. 4D using any suitable technique or techniques, e.g., polishing, grinding, chemical etching, reactive ion etching, etc. The package substrate 12 can have any suitable thickness, e.g., at least 10 micrometers and no greater than 900 micrometers.

Figure 4E:
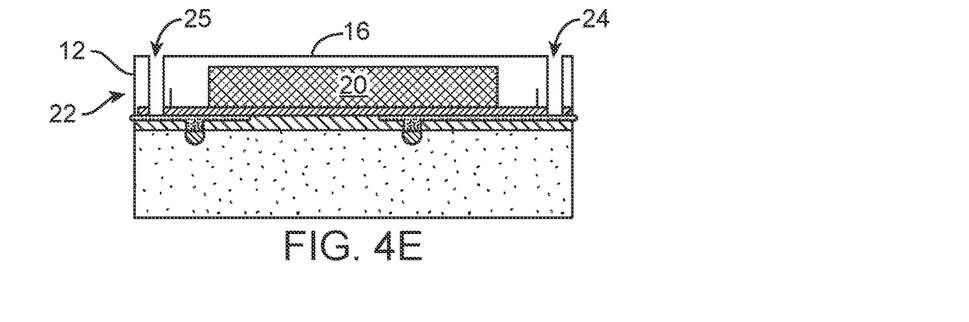
FIG. 4E is a schematic cross-section view of vias disposed in the package substrate.

As shown in FIG. 4E, one or more conductive vias such as vias 24, 25 can be disposed through the inactive region 22 of the substrate 12 using any suitable technique or techniques. For example, the vias 24, 25 can be disposed in the substrate 12 by etching, mechanical drilling, laser drilling, punching, etc.

Figure 4F:
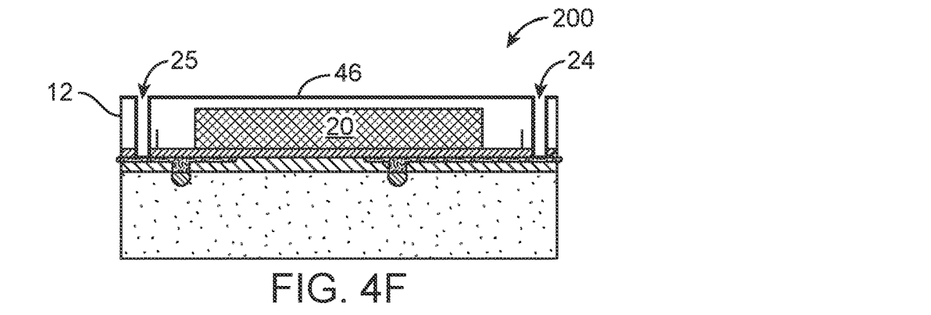
FIG. 4F is a schematic cross-section view of a dielectric material disposed on a second major surface of the package substrate and within the vias.

As shown in FIG. 4F, the dielectric layer 46 can be disposed on the second major surface 16 of the package substrate 12 and within one or more of the vias 24, 25 using any suitable technique or techniques.

Figure 4G:
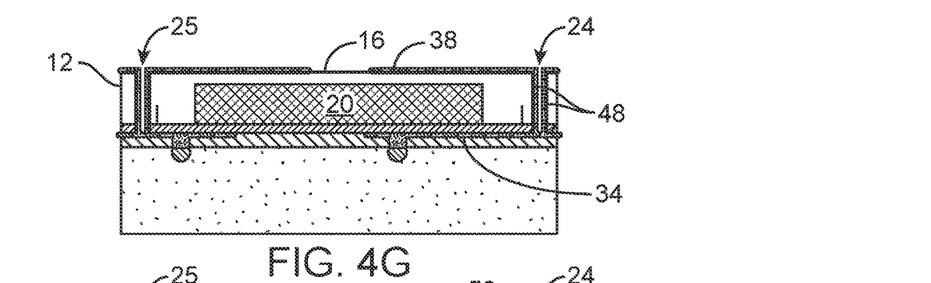
FIG. 4G is a schematic cross-section view of a conductive material disposed on the dielectric material.

The second patterned conductive layer 38 can be disposed adjacent to the second major surface 16 of the substrate 12 as shown in FIG. 4G. Any suitable technique or techniques can be utilized to dispose and pattern the second patterned conductive layer 38. Further, conductive material 48 can be disposed within at least one of the vias 24, 25 using any suitable technique or techniques. The conductive material 48 can be electrically connected to at least one of the patterned conductive layer 34 or the second patterned conductive layer 38. In one or more embodiments, the same processing step can be utilized to dispose the second patterned conductive layer 38 and the conductive material 48.

Figure 4H:
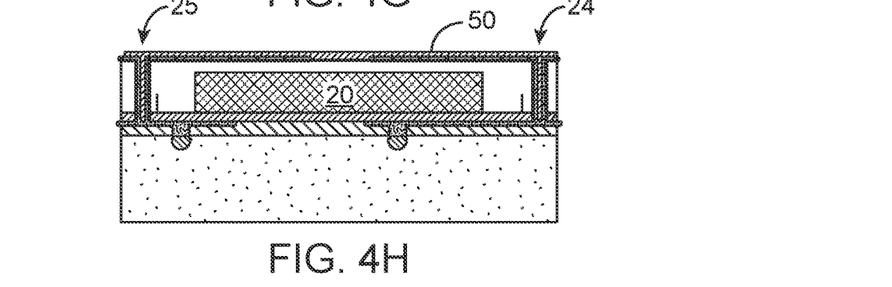
FIG. 4H is a schematic cross-section view of insulating material disposed on the conductive material.

In FIG. 4H, insulating material 50 can be disposed over the second patterned conductive layer 38 and within at least one of the vias 24, 25 using any suitable technique or techniques. The insulating material 50 can be utilized to form one or more dielectric layers on the second pattern conductive layer 38 and within the vias.

Figure 4I:
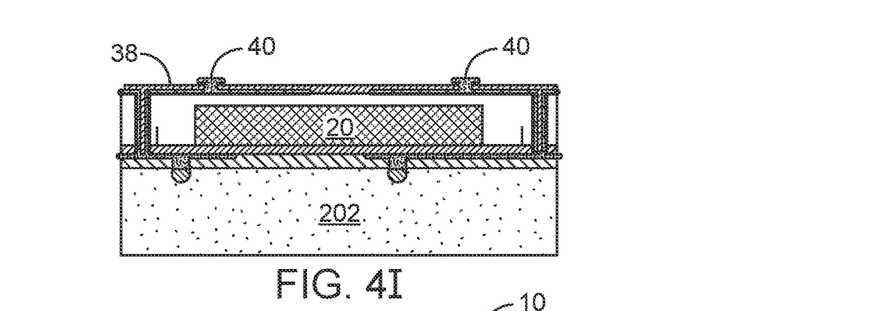
FIG. 4I is a schematic cross-section view of conductive pads or bumps disposed through the insulating material.

After the insulating material 50 is disposed on or over the second patterned conductive layer 38, one or more conductive pads 40 can be disposed in the insulating material such that they are electrically connected to the second patterned conductive layer 38 as shown in FIG. 4I. Any suitable technique or techniques can be utilized to dispose the conductive pads 40 in the insulating material 50. The conductive pads 40 can be utilized to connect the package 10 to one or more devices or packages.

Figure 4J:
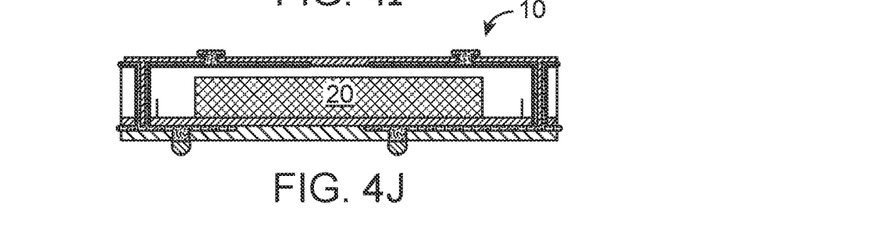
FIG. 4J is a schematic cross-section view of the carrier removed from the package.

As shown in FIG. 4J, the nonconductive carrier 202 can be removed from the package 10 using any suitable technique or techniques to provide the completed package. In embodiments where a plurality of electronic packages 10 are disposed on or within the wafer substrate 102 of wafer 100, the packages can be singulated to provide individual packages using any suitable technique or techniques, e.g., sawing, laser cracking and tape expansion (also called stealth dicing), plasma dicing, etc. In one or more embodiments, the packages 10 can be singulated along one or more singulation streets (e.g., singulation street 62 of FIG. 2).

The various embodiments of electronic packages described herein can be utilized in any suitable electronic system. For example, one or more embodiments of electronic packages described herein can be utilized in an IMD, ICD, IPG, insertable cardiac monitor, implantable diagnostic monitor, deep brain stimulator, implantable neurostimulator, injectable neurostimulator, implantable ventricular assist device, etc.

Figure 5:
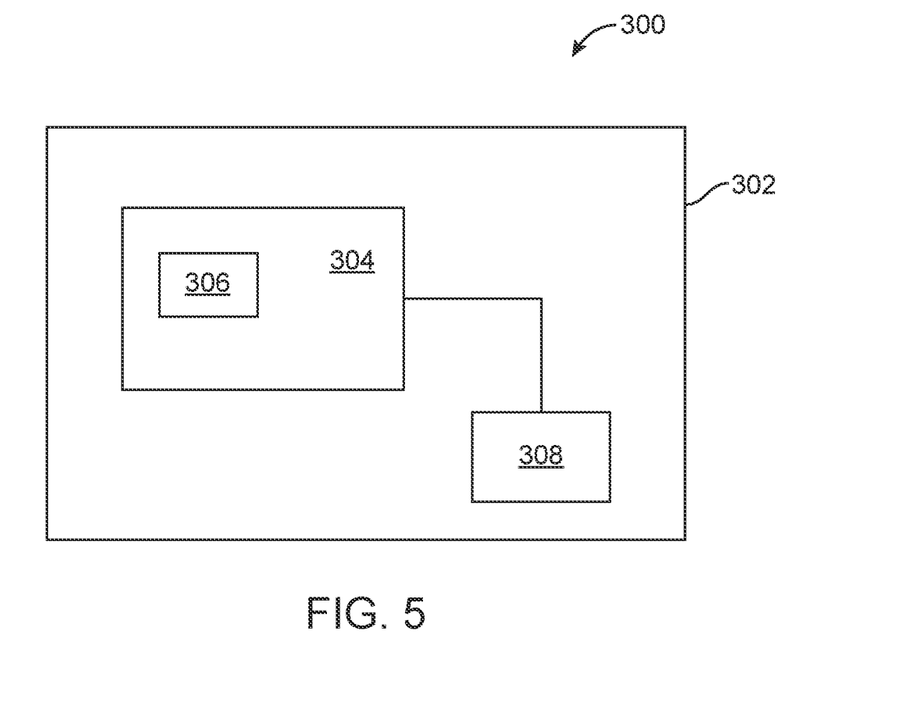
FIG. 5 is a schematic plan view of one embodiment of an implantable medical device that includes an electronic package.

FIG. 5 is a schematic plan view of one embodiment of an implantable medical device (IMD) 300. The IMD 300 includes a housing 302 and electronics module 304 disposed within the housing. The electronics module 304 can include any suitable electronic devices, e.g., at least one of a capacitor, resistor, passive integrated capacitor system, logic circuit, analog circuit, crystal, accelerometer, RF circuit, antenna, transformer, connector, etc. In one or more embodiments, the electronics module 304 includes an electronic package 306. The package 306 can include any suitable electronic package, e.g., electronic package 10 of FIGS. 1-2. The electronic package 306 can be electrically connected to other electronics modules 304 using any suitable technique or techniques. Also disposed within the housing 302 of the IMD is a power source 308 that is electrically connected to the electronics module 304 using any suitable technique or techniques. The power source 308 can include any suitable power source or combination of power sources, e.g., one or more batteries, capacitors, inductive-coupled energy devices, photovoltaic devices, betavoltaic devices, alphavoltaic devices, and thermo-electric devices.

Figure 6:
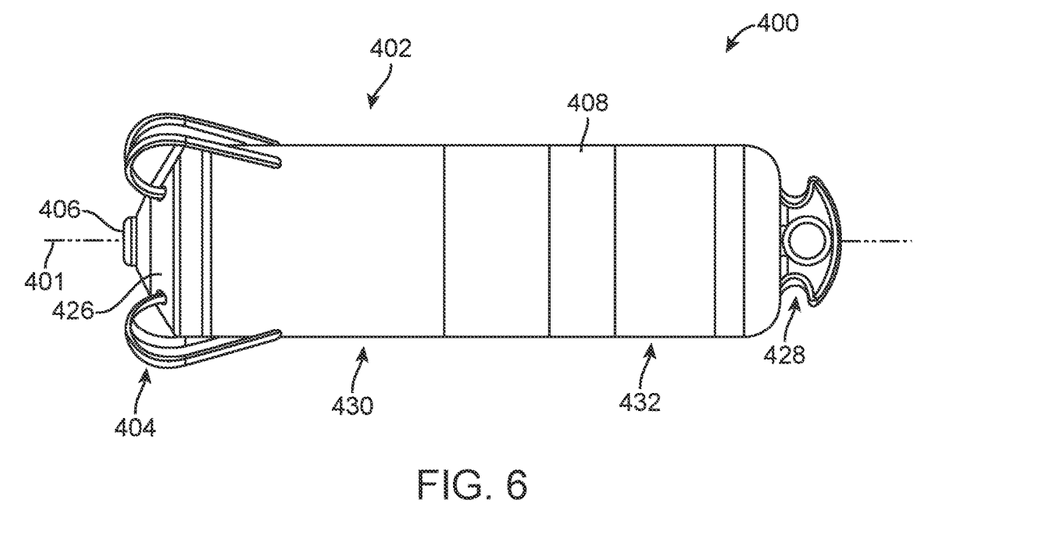
FIG. 6 is a schematic plan view of another embodiment of an implantable medical device that includes an electronic package.
Figure 7:
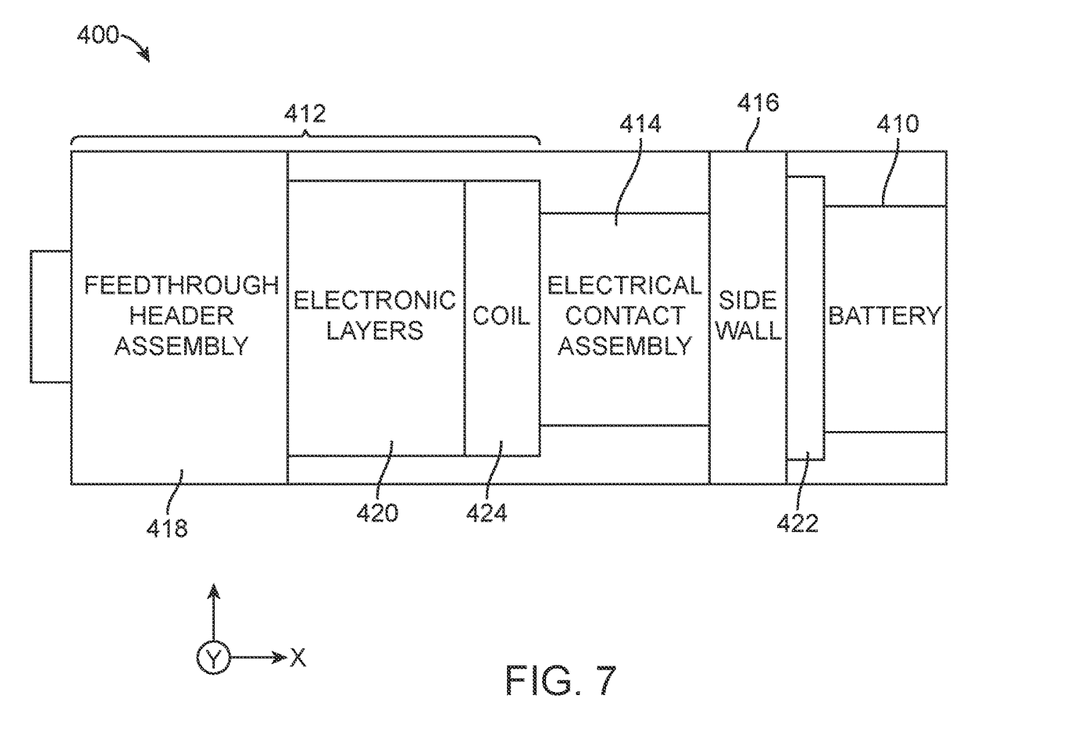
FIG. 7 is a schematic block diagram view of the implantable medical device of FIG. 6.

FIGS. 6-7 are various views of another embodiment of an implantable medical device 400 (IMD) that can include electronic package 10 of FIGS. 1-2. Although depicted as including package 10, the device 400 can include any suitable electronic package or packages.

In one or more embodiments, the IMD 400 is adapted to be implanted within a chamber of a heart of the patient, e.g., to monitor electrical activity of the heart and/or provide electrical therapy to the heart. The IMD 400 can include any suitable IMD, e.g., one or more embodiments of IMDs described in co-owned U.S. Patent Application No. 62/950,694 to Ries et al. entitled FEEDTHROUGH ASSEMBLY AND DEVICE INCLUDING SAME. In the example shown in FIGS. 6-7, the IMD 400 includes a housing 402, fixation tines 404, and electrodes 406 and 408.

Housing 402, also referred to as an elongated tubular housing, can extend between a first end 426 and a second end 428 along a longitudinal axis 401. A first portion 430 of the housing 402 is adjacent to the first end 426 and encloses an electronics module 412 (FIG. 7). Further, a second portion 432 of the housing 402 adjacent to the second end 428 encloses the power source (e.g., battery) 410. The housing 402 can house any suitable electronic components of the IMD 400, e.g., sensing circuitry for sensing electrical activity via electrodes 406 and 408 and therapy generation circuitry for delivering electrical stimulation therapy via the electrodes. Electronic components can include any discrete and/or integrated electronic circuit components that implement analog and/or digital circuits capable of producing the functions attributed to the IMD 400, e.g., electronic package 10 of FIGS. 1-2. In one or more embodiments, housing 402 can also house components for sensing other physiological parameters, such as acceleration, pressure, sound, and/or impedance. Although shown with two electrodes 406, 408, the device 400 can include any suitable number of electrodes disposed in any suitable portion or portions of the housing.

Additionally, the housing 402 can also house a memory that includes instructions that, when executed by processing circuitry housed within housing, cause the IMD 400 to perform various functions attributed to the device herein. In one or more embodiments, the housing 402 can house communication circuitry that enables the IMD 400 to communicate with other electronic devices, such as a medical device programmer. In one or more embodiments, the housing 402 can house an antenna for wireless communication. The housing 402 can also house a power source, such as a battery. The housing 402 can be hermetically or near-hermetically sealed using any suitable technique or techniques to help prevent fluid ingress into housing. For example, in one or more embodiments, one or more portions of the housing 402 can be hermetically sealed together utilizing one or more laser diffusion bonding techniques described in co-owned U.S. Pat. No. 10,124,559 B2, entitled KINETICALLY LIMITED NANO-SCALE DIFFUSION BOND STRUCTURES AND METHODS.

FIG. 7 is a schematic block diagram of the IMD 400 including the power source 410 (e.g., battery), the electronics module 412, and an electrical contact assembly 414. Although the IMD of FIG. 7 is described as IMD 400, the structures shown in FIG. 7 can also be used in other implantable or external medical devices, such as cardioverter-defibrillators, physiological monitors, or neurostimulators, or any other electronic devices. The IMD 400 also includes a feedthrough header assembly 418.

The housing 402 includes a side wall 416 disposed within the housing between the battery 410 and the electrical contact assembly 414. The side wall 416 can include at least one feedthrough (not shown) to allow for electrical connection between the battery 410 and the electronics module 412. The feedthrough header assembly 418 can also include at least one feedthrough to allow for an electrical connection between electrode 406 and electronic layers 420 of the electronics module 412. Electronics module 412 is disposed between the electrode 406 and electrical contact assembly 414. In one or more embodiments, electrical contact assembly 414 can be fixed to side wall 416 to provide mechanical support for the electronics module 412. The electrical contact assembly 414 provides an electrical connection between the battery 410 and the electronics module 412. The IMD 400 can also include a battery header 422 disposed between the battery 410 and the electrical contact assembly 414.

The electronics module 412 can include any suitable elements or components. For example, as shown in FIG. 7, the electronics module 412 includes one or more electronic layers 420 and the feedthrough header assembly 418 electrically connected to the one or more electronic layers. The electronics module 412 can also include one or more coils 424 electrically connected to the electronic layers 420.

The electronic layers 420 can include any suitable electronic devices or packages. In one or more embodiments, the electronic layers 420 can include one or more electronic packages, e.g., electronic package 10 of FIGS. 1-2.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable medical device comprising:
a power source;
an electronics module comprising an electronic package that comprises:
a monolithic package substrate comprising a first major surface and a second major surface;
an integrated circuit disposed in an active region of the package substrate; and
a conductive via disposed through an inactive region of the package substrate and extending between the first major surface and the second major surface of the package substrate, wherein the conductive via is separated from the active region by a portion of the inactive region of the substrate; and
a feedthrough header assembly electrically connected to the electronics module.

2. The device of claim 1, further comprising an elongated tubular housing extending between a first end and a second end along a longitudinal axis, wherein a first portion of the housing adjacent to the first end encloses the electronics module and a second portion of the housing adjacent to the second end encloses the power source.

3. The device of claim 1, wherein the active region of the electronic package takes a rectangular shape in a plane parallel to the first major surface of the package substrate, wherein the inactive region further comprises a second portion, wherein the portion and second portion of the inactive region are disposed on opposing sides of the active region in the plane parallel to the first major surface of the package substrate.

4. The device of claim 3, wherein the electronic package further comprises a second conductive via disposed through the inactive region of the package substrate and extending between the first major surface and the second major surface of the package substrate, wherein the second conductive via is separated from the active region by the second portion of the inactive region of the substrate.

5. The device of claim 1, wherein the electronic package further comprises a patterned conductive layer disposed adjacent to at least one of the first major surface or the second major surface of the package substrate and electrically connected to the conductive via and the integrated circuit.

6. The device of claim 5, wherein the patterned conductive layer is disposed adjacent to the first major surface of the substrate, wherein the electronic package further comprises a second patterned conductive layer disposed adjacent to the second major surface of the substrate and electrically connected to the conductive via.

7. The device of claim 6, wherein the electronic package further comprises a dielectric layer disposed between the patterned conductive layer and the first major surface of the package substrate.

8. The device of claim 7, wherein the electronic package further comprises a dielectric layer disposed between the second patterned conductive layer and the second major surface of the package substrate.

9. The device of claim 1, wherein the active region of the integrated circuit of the electronic package is embedded within the inactive region of the package substrate such that the active region is surround by the inactive region in a plane parallel to the first major surface of the package substrate.

10. The device of claim 1, wherein the conductive via of the electronic package extends in a direction substantially orthogonal to the first and second major surfaces of the substrate.

11. The device of claim 1, wherein the electronic package further comprises a guard ring disposed in the first major surface of substrate, wherein the guard ring circumscribes the active region and the integrated circuit.

12. The device of claim 1, wherein the conductive via of the electronic package comprises a dielectric layer disposed on one or more walls of the via.

13. The device of claim 12, wherein the conductive via of the electronic package further comprises conductive material disposed in the via such that the dielectric material is between the conductive material and the one or more walls of the via.

14. The device of claim 13, wherein the conductive via of the electronic package further comprises insulating material disposed within the via such that the conductive material is disposed between the one or more walls of the via and the insulating material.

15. The device of claim 1, wherein the integrated circuit of the electronic package comprises at least one of a field effect transistor (FET), metal oxide semiconductor (MOS), MOSFET, insulated gate bipolar junction transistor (IGBT), thyristor, bipolar transistor, diode, MOS-controlled thyristor, resistor, capacitor, inductor, sensor-mixed signal application-specific integrated circuit (ASIC), digital circuit, or analog circuit.

16. The device of claim 1, wherein the electronic package further comprises a conductive pillar disposed within the conductive via and electrically connected to the integrated circuit.

17. The device of claim 1, wherein the electronic package further comprises a conductive pad disposed on either the first major surface or the second major surface of the substrate and electrically connected to the integrated circuit.

18. The device of claim 1, wherein the electronics module further comprises a feedthrough header assembly electrically connected to one or more electronic layers of the electronics module.

19. The device of claim 18, further comprising an electrode electrically connected to the one or more electronic layers of the electronics module by a feedthrough header assembly.

20. The device of claim 1, further comprising an electrical contact assembly disposed between the power source and the electronics module and configured to provide an electrical connection between the power source and the electronics module.

* * * * *